(12) United States Patent
Aali

(10) Patent No.: US 7,816,577 B2
(45) Date of Patent: *Oct. 19, 2010

(54) WOUND SHIELD

(75) Inventor: Adel Aali, Irvine, CA (US)

(73) Assignee: Aalnex, Inc., Irvine, CA (US)

( * ) Notice: Subject to any disclaimer, the term of this patent is extended or adjusted under 35 U.S.C. 154(b) by 158 days.

This patent is subject to a terminal disclaimer.

(21) Appl. No.: 11/707,464

(22) Filed: Feb. 12, 2007

(65) Prior Publication Data

US 2007/0191754 A1 Aug. 16, 2007

Related U.S. Application Data

(60) Provisional application No. 60/773,252, filed on Feb. 13, 2006.

(51) Int. Cl.
*A61F 15/00* (2006.01)
*A61F 13/00* (2006.01)

(52) U.S. Cl. .................. 602/58; 604/304; 128/888

(58) Field of Classification Search .......... 602/41, 602/42, 56–58, 2; 604/304, 307; 607/96, 607/97, 108–112; 128/888–889
See application file for complete search history.

(56) References Cited

U.S. PATENT DOCUMENTS

| | | | | |
|---|---|---|---|---|
| 2,273,873 A | 2/1942 | Klein | ............ | 128/888 |
| 2,305,289 A | 12/1942 | Coburg | | |
| 2,367,690 A | 1/1945 | Purdy | ............ | 128/888 |
| 2,443,140 A | 6/1948 | Larsen | ............ | 128/888 |
| 2,443,481 A | 6/1948 | Sene | ............ | 128/888 |
| 3,026,874 A * | 3/1962 | Stevens | ............ | 604/305 |
| 3,334,626 A | 8/1967 | Schimmel | ............ | 128/888 |
| 4,023,569 A | 5/1977 | Warnecke et al. | ............ | 128/154 |
| 4,181,127 A | 1/1980 | Linsky et al. | ............ | 602/43 |
| 4,212,296 A | 7/1980 | Schaar | ............ | 602/42 |
| 4,252,120 A | 2/1981 | Carpenter | | |
| 4,726,364 A | 2/1988 | Wylan | ............ | 602/44 |
| 4,969,881 A * | 11/1990 | Viesturs | ............ | 604/305 |
| 4,972,829 A | 11/1990 | Knerr | | |
| 5,020,547 A | 6/1991 | Strock | | |
| 5,060,662 A * | 10/1991 | Farnswoth, III | ............ | 128/888 |
| 5,086,763 A | 2/1992 | Hathman | | |
| 5,101,837 A | 4/1992 | Perrin | ............ | 128/888 |
| 5,215,539 A | 6/1993 | Schoolman | | |

(Continued)

FOREIGN PATENT DOCUMENTS

DE 1963375 A1 6/1971

(Continued)

OTHER PUBLICATIONS

USPTO Notice of Allowance for U.S. Appl. No. 11/409,364, 7 pages (mailed Jul. 10, 2009).

(Continued)

*Primary Examiner*—Patricia M Bianco
*Assistant Examiner*—Tarla R Patel
(74) *Attorney, Agent, or Firm*—Jones Day; Nicola A. Pisano; Christopher C. Bolten

(57) ABSTRACT

A preformed wound shield includes a frame formed of one or more layers of suitable material and any suitable covering. Exudate absorbing or transporting material may also be one of two or more layers of material forming the frame.

10 Claims, 11 Drawing Sheets

U.S. PATENT DOCUMENTS

| | | | |
|---|---|---|---|
| 5,264,218 A | 11/1993 | Rogozinski | |
| 5,356,372 A | 10/1994 | Donovan et al. | 602/58 |
| 5,376,067 A | 12/1994 | Daneshvar | 602/58 |
| 5,449,340 A | 9/1995 | Tollini | |
| 5,456,660 A | 10/1995 | Reich et al. | |
| 5,478,308 A | 12/1995 | Cartmell et al. | |
| 5,527,265 A | 6/1996 | McKeel | 602/6 |
| 5,533,962 A | 7/1996 | Peterman et al. | 602/54 |
| 5,603,946 A | 2/1997 | Constantine | |
| 5,695,456 A | 12/1997 | Cartmell et al. | |
| 5,702,356 A | 12/1997 | Hathman | |
| 5,817,145 A | 10/1998 | Augustine et al. | 607/98 |
| 5,843,011 A | 12/1998 | Lucas | |
| 5,885,237 A | 3/1999 | Kadash et al. | |
| 5,891,074 A | 4/1999 | Cesarczyk | 602/42 |
| 5,947,914 A | 9/1999 | Augustine | 602/2 |
| 5,954,680 A | 9/1999 | Augustine | 602/42 |
| 5,961,480 A | 10/1999 | Augustine | 602/41 |
| 5,964,721 A | 10/1999 | Augustine | 602/2 |
| 5,964,723 A | 10/1999 | Augustine | 602/42 |
| 5,986,163 A | 11/1999 | Augustine | 712/204 |
| 6,000,403 A | 12/1999 | Cantwell | |
| 6,005,159 A | 12/1999 | Spier | 602/42 |
| 6,010,527 A | 1/2000 | Augustine et al. | 607/96 |
| 6,013,097 A | 1/2000 | Augustine et al. | 607/96 |
| 6,043,408 A | 3/2000 | Geng | 602/58 |
| 6,045,518 A | 4/2000 | Augustine | 602/2 |
| 6,071,254 A | 6/2000 | Augustine | 602/2 |
| 6,071,304 A | 6/2000 | Augustine et al. | 607/96 |
| 6,080,189 A | 6/2000 | Augustine et al. | 607/96 |
| 6,093,160 A | 7/2000 | Augustine et al. | 602/2 |
| 6,095,992 A | 8/2000 | Augustine | 464/24 |
| 6,110,197 A | 8/2000 | Augustine et al. | 607/108 |
| 6,113,561 A | 9/2000 | Augustine | 602/2 |
| 6,143,945 A | 11/2000 | Augustine et al. | 602/41 |
| 6,168,800 B1 | 1/2001 | Dobos et al. | |
| 6,213,965 B1 | 4/2001 | Augustine et al. | 602/2 |
| 6,213,966 B1 | 4/2001 | Augustine | 602/2 |
| 6,217,535 B1 | 4/2001 | Augustine | 602/2 |
| 6,235,047 B1 | 5/2001 | Augustine et al. | 607/96 |
| 6,267,740 B1 | 7/2001 | Augustine et al. | 602/2 |
| 6,283,931 B1 | 9/2001 | Augustine | 602/2 |
| 6,293,917 B1 | 9/2001 | Augustine | 602/2 |
| 6,320,093 B1 | 11/2001 | Augustine et al. | 602/41 |
| 6,323,386 B1 | 11/2001 | Stapf et al. | 602/41 |
| 6,406,448 B1 | 6/2002 | Augustine | 602/2 |
| 6,407,307 B1 | 6/2002 | Augustine | 602/2 |
| 6,419,651 B1 | 7/2002 | Augustine | 602/2 |
| 6,420,622 B1 | 7/2002 | Johnston et al. | 602/41 |
| 6,420,623 B2 | 7/2002 | Augustine et al. | 602/41 |
| 6,423,018 B1 | 7/2002 | Augustine | 602/2 |
| 6,426,066 B1 | 7/2002 | Najafi et al. | 424/78.04 |
| 6,436,063 B1 | 8/2002 | Augustine et al. | 602/2 |
| 6,440,156 B1 | 8/2002 | Augustine et al. | 607/96 |
| 6,458,109 B1 | 10/2002 | Henley et al. | |
| 6,465,708 B1 | 10/2002 | Augustine | 602/42 |
| 6,468,295 B2 | 10/2002 | Augustine et al. | 607/96 |
| 6,485,506 B2 | 11/2002 | Augustine | 607/96 |
| 6,528,697 B1 | 3/2003 | Knutson et al. | 602/54 |
| 6,569,189 B1 | 5/2003 | Augustine et al. | 607/96 |
| 6,570,050 B2 | 5/2003 | Augustine et al. | 602/41 |
| 6,573,420 B2 | 6/2003 | Stapf et al. | 602/42 |
| 6,580,012 B1 * | 6/2003 | Augustine et al. | 602/42 |
| 6,585,670 B2 | 7/2003 | Augustine et al. | 602/2 |
| 6,589,270 B2 | 7/2003 | Augustine | 607/96 |
| 6,605,051 B2 | 8/2003 | Augustine | 602/2 |
| 6,626,891 B2 | 9/2003 | Ohmstede | |
| 6,641,601 B1 | 11/2003 | Augustine et al. | 607/96 |
| 6,653,520 B1 | 11/2003 | Mouton | 602/45 |
| 6,685,681 B2 | 2/2004 | Lockwood et al. | |
| 6,716,235 B2 | 4/2004 | Augustine et al. | 607/96 |
| 6,840,915 B2 | 1/2005 | Augustine | 602/2 |
| 6,921,374 B2 | 7/2005 | Augustine | 602/2 |
| 6,960,181 B2 | 11/2005 | Stevens | |
| 6,974,428 B2 | 12/2005 | Knutson et al. | 602/2 |
| 7,012,170 B1 | 3/2006 | Tomaioulo | |
| 7,074,982 B2 | 7/2006 | Knutson et al. | 602/42 |
| 7,112,712 B1 | 9/2006 | Ancell | |
| 7,118,545 B2 | 10/2006 | Boyde | 602/79 |
| 7,122,046 B2 | 10/2006 | Augustine et al. | 607/96 |
| 7,122,712 B2 | 10/2006 | Lutri et al. | 602/43 |
| 7,135,606 B1 | 11/2006 | Dozier et al. | 602/57 |
| 7,176,343 B2 | 2/2007 | Schlussel | |
| 7,183,454 B1 * | 2/2007 | Rosenberg | 602/43 |
| 7,276,051 B1 * | 10/2007 | Henley et al. | 604/304 |
| 7,601,129 B2 | 10/2009 | Aali | |
| 7,622,629 B2 | 11/2009 | Aali | |
| 2002/0007136 A1 | 1/2002 | Narula et al. | 602/46 |
| 2002/0026133 A1 | 2/2002 | Augustine et al. | 607/2 |
| 2002/0029010 A1 * | 3/2002 | Augustine et al. | 602/41 |
| 2003/0036715 A1 | 2/2003 | Knutson et al. | |
| 2003/0088201 A1 | 5/2003 | Darcey | 602/44 |
| 2004/0249328 A1 | 12/2004 | Linnane et al. | 602/43 |
| 2005/0004500 A1 * | 1/2005 | Rosser et al. | 602/41 |
| 2005/0010153 A1 * | 1/2005 | Lockwood et al. | 602/41 |
| 2005/0070835 A1 * | 3/2005 | Joshi | 602/41 |
| 2005/0107732 A1 | 5/2005 | Boyde | |
| 2005/0113731 A1 | 5/2005 | Qvist | 602/48 |
| 2005/0148921 A1 | 7/2005 | Hsu | 602/48 |
| 2005/0222528 A1 * | 10/2005 | Weston | 602/1 |
| 2006/0064049 A1 | 3/2006 | Marcussen | 602/42 |
| 2006/0116620 A1 * | 6/2006 | Oyaski | 602/42 |
| 2006/0189909 A1 | 8/2006 | Hurley et al. | 602/41 |
| 2006/0235347 A1 | 10/2006 | Aali | |
| 2006/0253089 A1 | 11/2006 | Lin | 604/301 |
| 2007/0142757 A1 | 6/2007 | Aali | |
| 2007/0142761 A1 * | 6/2007 | Aali | 602/42 |
| 2007/0161937 A1 | 7/2007 | Aali | |
| 2007/0161938 A1 | 7/2007 | Aali | |
| 2007/0191754 A1 | 8/2007 | Aali | |

FOREIGN PATENT DOCUMENTS

| | | |
|---|---|---|
| EP | 0117714 A2 | 9/1984 |
| WO | WO 85/01439 A1 | 4/1985 |
| WO | WO 96/15745 A1 | 5/1996 |
| WO | WO98/53778 | 12/1998 |

OTHER PUBLICATIONS

USPTO Final Office Action for U.S. Appl. No. 11/409,364, 9 pages (mailed Mar. 10, 2009).

USPTO Non-Final Office Action for U.S. Appl. No. 11/409,364, 7 pages (mailed May 22, 2008).

USPTO Advisory Action for U.S. Appl. No. 11/409,364, 3 pages (mailed Apr. 8, 2008).

USPTO Final Office Action for U.S. Appl. No. 11/409,364, 7 pages (mailed Nov. 30, 2007).

USPTO Non-Final Office Action for U.S. Appl. No. 11/409,364, 7 pages (mailed May 31, 2007).

USPTO Non-Final Office Action for U.S. Appl. No. 11/303,463, 10 pages (mailed Mar. 17, 2009).

USPTO Final Office Action for U.S. Appl. No. 11/303,463, 9 pages (mailed Dec. 26, 2008).

USPTO Non-Final Office Action for U.S. Appl. No. 11/303,463, 11 pages (mailed Mar. 18, 2008).

USPTO Non-Final Office Action for U.S. Appl. No. 11/107,452, 11 pages (mailed Mar. 17, 2009).

USPTO Final Office Action for U.S. Appl. No. 11/107,452, 8 pages (mailed Sep. 19, 2008).

USPTO Non-Final Office Action for U.S. Appl. No. 11/107,452, 7 pages (mailed Dec. 4, 2007).

USPTO Non-Final Office Action for U.S. Appl. No. 11/107,452, 8 pages (mailed May 31, 2007).

USPTO Notice of Allowance for U.S. Appl. No. 11/303,155, 5 pages (mailed Jun. 12, 2009).

USPTO Non-Final Office Action for U.S. Appl. No. 11/303,155, 7 pages (mailed Jan. 8, 2009).

USPTO Non-Final Office Action for U.S. Appl. No. 11/303,155, 9 pages (mailed Jul. 14, 2008).

USPTO Final Office Action for U.S. Appl. No. 11/441,702, 12 pages (mailed Apr. 10, 2009).

USPTO Non-Final Office Action for U.S. Appl. No. 11/441,702, 8 pages (mailed Jun. 26, 2008).

USPTO Non-Final Office Action for U.S. Appl. No. 11/441,702, 9 pages (mailed May 1, 2007).

USPTO Final Office Action for U.S. Appl. No. 11/303,463, 10 pages (mailed Apr. 8, 2010).

USPTO Examiner Interview Summary and Non-Final Office Action for U.S. Appl. No. 11/303,463, 9 pages (mailed Aug. 20, 2009).

USPTO Notice of Allowance for U.S. Appl. No. 11/107,452, 5 pages (mailed Apr. 29, 2010).

USPTO Final Office Action for U.S. Appl. No. 11/107,452, 8 pages (mailed Dec. 24, 2009).

USPTO Notice of Allowance for U.S. Appl. No. 11/441,702, 4 pages (mailed Apr. 12, 2010).

USPTO Non-Final Office Action for U.S. Appl. No. 11/441,702, 7 pages (mailed Oct. 27, 2009).

* cited by examiner

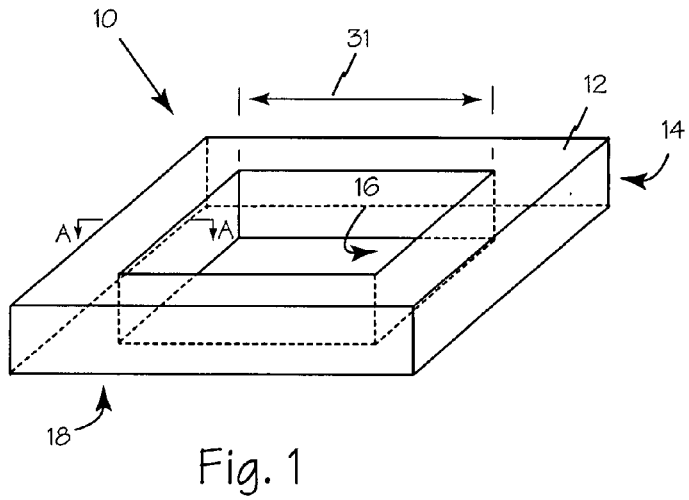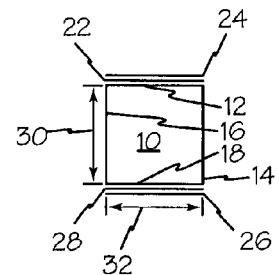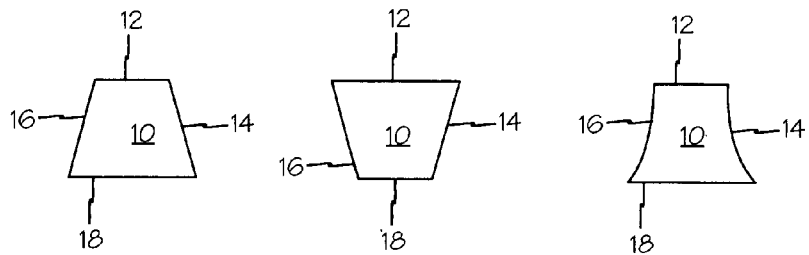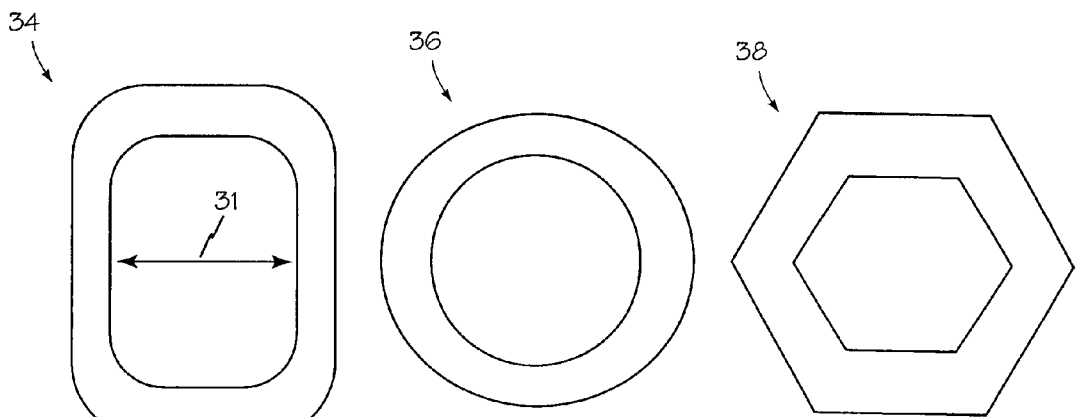

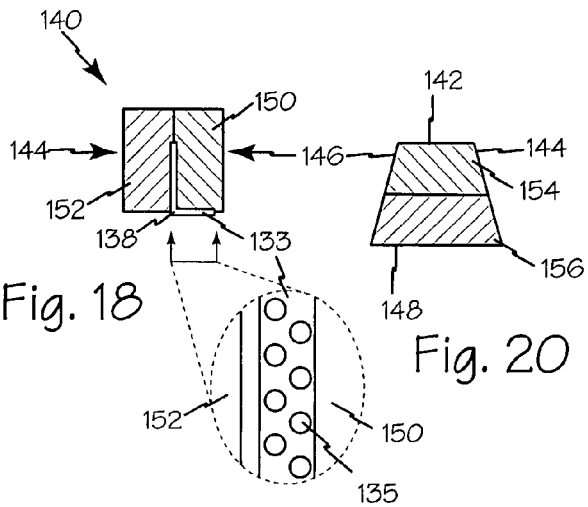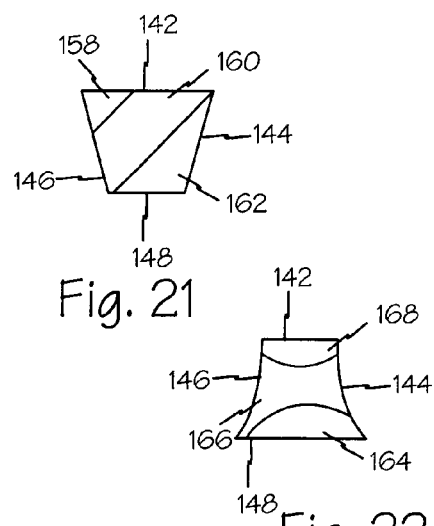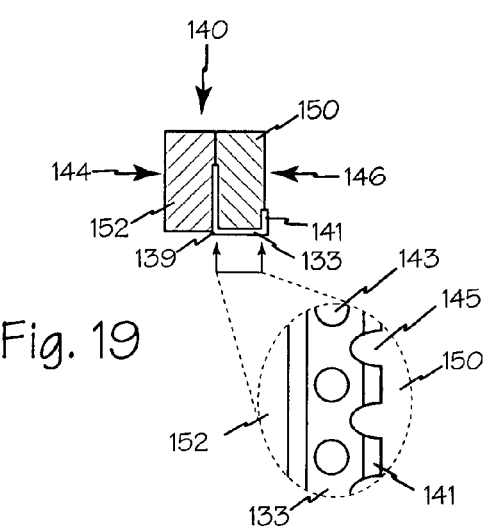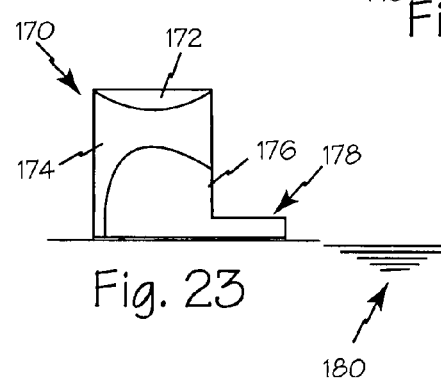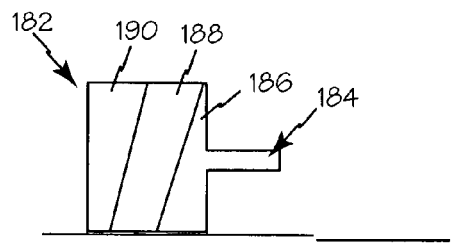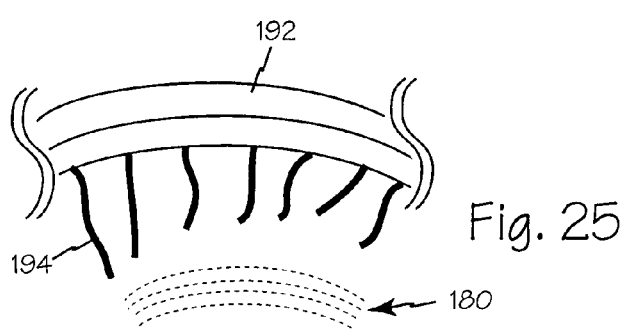

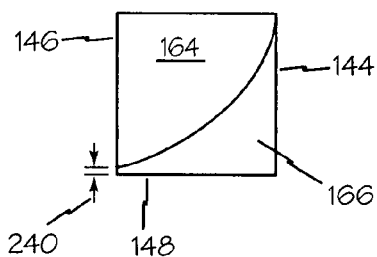 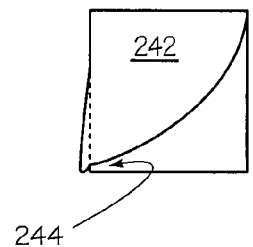
Fig. 31    Fig. 32
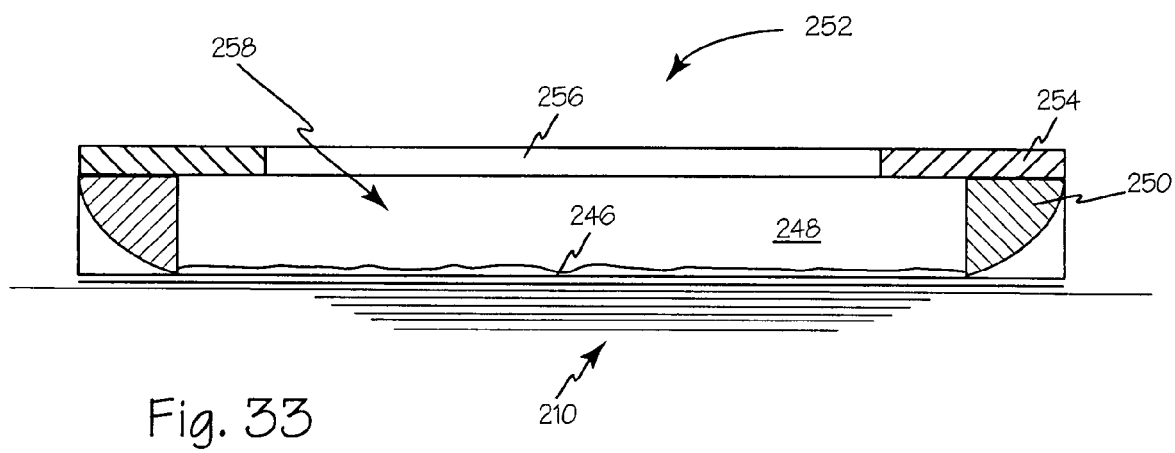
Fig. 33

WOUND SHIELD

RELATED APPLICATIONS

This application claims priority to copending U.S. Provisional Patent Application 60/773,252 filed Feb. 13, 2006.

FIELD OF THE INVENTIONS

The inventions described below relate to the field of wound care management.

BACKGROUND OF THE INVENTIONS

Wounds occur when the integrity of any tissue is compromised, affecting one or more layers of skin or underlying tissue. Wounds may be caused by an act, surgical procedure, an infectious disease or an underlying condition. Examples of open wounds include punctures, abrasions, cuts, lacerations and burns. Chronic wounds are also common ailments and include pressure ulcers, diabetic ulcers, arterial ulcers, venous ulcers or combination of all the above. Despite much progress made in the wound care industry, an efficient and effective method and apparatus for protecting the wound from injurious contacts is not readily available.

Injurious contacts with foreign objects may be caused from various sources, ranging from brushing of clothing or bed sheets to fresh, uncovered wounds to adherence of wound dressing to the wound. The latter issue, referred to here as the sticking issue, leads to deleterious consequences for the patient. This problem is particularly exacerbated when wounds are left unattended for a substantial period. It is reported that in certain circumstances patients are administered morphine to withstand the pain caused from dressing removal, especially with wounds having a large surface area. Equally important, tearing of skin graft, newly formed cells or scab adhered to dressing disrupts the healing process.

Wounds are generally covered to prevent contamination and resulting infection. Wounds may also be covered for other reasons, including retaining moisture and absorption of exudate. Wound covering has traditionally consisted of application of dressings that are in direct contact with the wound. When directly applied on the wound, dressings adhere and mechanically anchor to wound surface, which may include diffused wound fluid, skin graft, new epidermal cells forming over the wound or the scabby covering of the wound.

The sticking issue has traditionally been addressed by soaking the wound and the dressing adhering to it in water for some time to soften the scab and make removal easier. Another method is the application of antibiotic ointments, such as polymyxin B sulfate or bacitracin, to keep the bandage from sticking to the wound. These methods, however, have not sufficiently addressed the sticking issue. As can be appreciated by health care professionals, soaking in water or application of ointments are not always practicable or recommended.

To better address the sticking issue the medical industry has developed "non-stick" dressings such as Telfa® and Xeroform® and other dressings such as hydrocolloids, alginates, hydrofilms, etc. Non-stick, however, is a relative term. Non-stick dressings merely stick less than their traditional counterparts, e.g., cotton gauze. Another problem with these dressings is that their cost is prohibitive for use on wounds requiring constant change of dressing.

Similar to the traditional and "non-stick" dressings described above, conventional "non-contact" dressings also fail to efficiently and effectively protect the wound from contact, including addressing the sticking issue. Conventional non-contact dressings are also generally bulky, complicated to apply having too many subparts, unable to manage exudate, unable to manage moisture, generally inflexible and expensive.

What is needed is a method and apparatus for dressing wounds or other suitable injuries that is flexible to prevent contact with the surface of the wound, permit management of exudate from the wound and improve the environment immediately adjacent the wound.

SUMMARY

A wound shield includes a frame formed of one or more layers of suitable material and any suitable covering. Exudate absorbing material may also be one of two or more layers of material forming the frame. The layers may be arranged to keep the exudate absorbing layer at some selected distance from a patient's skin. Any suitable dressing may be secured over the frame providing separation between the wound and the dressing. The wound frame may provide pressure relief around a wound or pressure sore to permit healing. A frame may be composed of one or more layers of any suitable material and may include adhesive on one or more surfaces to secure the frame to the wound site and or to secure the dressing to the frame. One layer of the two or more layers of material forming the frame may be a wicking or conduit material that draws exudate from the wound and transports the exudate to any suitable media for exudate storage. The exudate storage may be one or more layers of a dressing covering the wound site, or it may be a removable reservoir.

A wound shield for exudate management may include a frame to circumscribe a wound. Any suitable dressing may be secured over the frame providing separation between the wound and the dressing. The wound frame may provide pressure relief around a wound or pressure sore to permit healing. A frame may be composed of one or more layers of any suitable material and may include adhesive on one or more surfaces to secure the frame to the wound site and or to secure the dressing to the frame.

Exudate as used in this application may also include any solid or liquid produced by the patient's body, or applied to or into a patients body that sloughs, falls, flows, or is discharged from a wound, the wound site or the tissue surrounding the wound.

In another aspect of the present disclosure, a frame may be formed of material for absorbing wound exudate. Exudate absorbing material may also be one of two or more layers of material forming the frame. The layers may be arranged to keep the exudate absorbing layer at some selected distance from a patients skin.

A wound shield for dynamic exudate management may include two or more layers of material. One layer of the two or more layers of material may be a wicking or conduit material that draws exudate from the wound and transports the exudate to any suitable media for exudate storage. The exudate storage may be one or more layers of a dressing covering the wound site, or it may be a removable reservoir.

A wound shield for exudate management may also include an exterior membrane to permit exudate transfer out of the wound space. A wound shield including an exterior membrane may also include an exudate collection apparatus surrounding the wound shield for collecting and removing exudate from the wound shield and from the patient.

A wound shield for exudate management may also include one or more reclosable or self-closing apertures in the frame to enable exudate management. The exudate aperture may be engaged as often as necessary for suitable wound care.

A wound shield may include a frame to circumscribe a wound. Any suitable dressing may be secured over the frame, the frame providing separation between the wound and the dressing. The wound frame may provide pressure relief around a wound or pressure sore to permit healing, allow compression for venous ulcers, retain moisture within the wound environment, absorb exudate, relieve pain and trauma associated with dressing removal, allow debridement and application of topical medications and or other compounds or chemicals, accelerate healing and facilitate monitoring of wounds. A frame may be composed of one or more layers of any suitable material and may include adhesive on one or more surfaces to secure the frame to the wound site and or to secure the dressing to the frame. A wound shield may be used for humans or any suitable animal.

A wound shield according to the present disclosure may be a simple, versatile, inexpensive and readily applicable apparatus and method for wound protection. It may include a wound-protecting frame that may adapt to the contour of the wound site and may be used with any suitable dressing. A wound shield prevents foreign objects such as clothing, dressings and other such items from contacting the wound. Cotton gauze or other suitable dressing may be placed on or engage a wound protecting frame to completely protect the wound from harmful contact with any object. Alternatively, special covers, seals, and or lids may be placed on the wound shield to control moisture, simplify wound monitoring and debridement and application of medications.

A wound shield according to the present disclosure may adhere to skin surrounding a wound via adhesive applied to a surface of the wound-protecting frame to engage the skin. Medical grade, hypoallergenic adhesives are preferred, although any suitable adhesive may be used such as rubber-based, acrylic, vinyl ether and suitable pressure-sensitive adhesives. For their obvious advantages, adhesives that adhere to body hair less than their conventional counterparts are preferred. Adhesives may also be added to one or more surfaces of a wound-protecting frame not in contact with skin to engage any suitable dressing, cover, lid or any other suitable closure. Alternatively, no adhesive is required to secure the wound shield to a patient, and the wound shield may be retained in place by the pressure applied from the dressing wrapped around the wound.

In use, a frame is placed around a wound, creating a boundary and providing a plane separate from the plane of the wound to support the dressing. A wound shield according to the present disclosure may adapt to the contours of a wound site located on any surface of a body. In addition, the frame may be made of inexpensive material.

Any suitable dressing may be used in conjunction with the frame, and may range from inexpensive, commonly used cotton gauze to more costly and sophisticated dressings, including for example, those constructed from transparent and or multi-layered material with qualities such as exudate absorption, bacteria impermeability and controlled air and or moisture permeability. Health care professionals may mix and match various dressings without restriction to complex and/or costly non-contact dressings.

A wound shield according to the present disclosure has sufficient rigidity to prevent injurious contacts to the wound, including those caused by dressing adhering to the wound surface. The frame prevents contact to wounds regardless of their size or location with any suitable dressing.

A wound shield according to the present disclosure may be used for swift and effective wound debridement using any suitable technique. For example, a wound shield may be used to create a controlled space adjacent a wound for biological debridement, use of maggots or other suitable techniques. Alternatively, mechanical and or chemical debridement may also be effected within the controlled space. Surgical debridement may also be performed without removing the frame from around the wound. The wound shield minimizes wound and peri-wound disturbance by avoiding repetitive dressing removals with the associated wound surface disturbance.

A wound shield including a frame to circumscribe a wound may also include a circulating system for circulating any suitable fluid to maintain a desired environment. Any suitable dressing may be secured over the frame providing separation between the wound and the dressing. The wound frame may provide pressure relief around a wound or pressure sore to permit healing. A frame may be composed of one or more layers of any suitable material and may include adhesive on one or more surfaces to secure the frame to the wound site and or to secure the dressing to the frame.

BRIEF DESCRIPTION OF THE DRAWINGS

FIG. 1 is a perspective view of a frame according to the present disclosure.

FIG. 2 is a cross section of the frame of FIG. 1 taken along A-A.

FIG. 3 is an alternate cross section of the frame of FIG. 1.

FIG. 4 is another alternate cross section of the frame of FIG. 1.

FIG. 5 is a still alternate cross section of the frame of FIG. 1.

FIG. 6 is a top view of an alternate frame according to the present disclosure.

FIG. 7 is a top view of another alternate frame according to the present disclosure.

FIG. 8 is a top view of yet another alternate frame according to the present disclosure.

FIG. 18 is a cross section of the frame of FIG. 17 taken along C-C.

FIG. 19 is a cross section of the frame of FIG. 17 taken along C-C with an alternate scaffold.

FIG. 20 is an alternate cross section of the frame of FIG. 17.

FIG. 21 is another alternate cross section of the frame of FIG. 17.

FIG. 22 is yet another alternate cross-section of the frame of FIG. 17.

FIG. 23 is an alternate cross section of the frame of FIG. 17 with a wicking element.

FIG. 24 is another alternate cross section of the frame of FIG. 23.

FIG. 25 is a perspective view of an alternate frame according to the present disclosure.

FIG. 31 is another still alternate cross section of the frame of FIG. 17.

FIG. 32 is yet another still alternate cross-section of the frame of FIG. 17.

FIG. 33 is a cross section of yet another alternate frame configuration with an absorbent dressing.

DETAILED DESCRIPTION OF THE INVENTIONS

Figure 9:
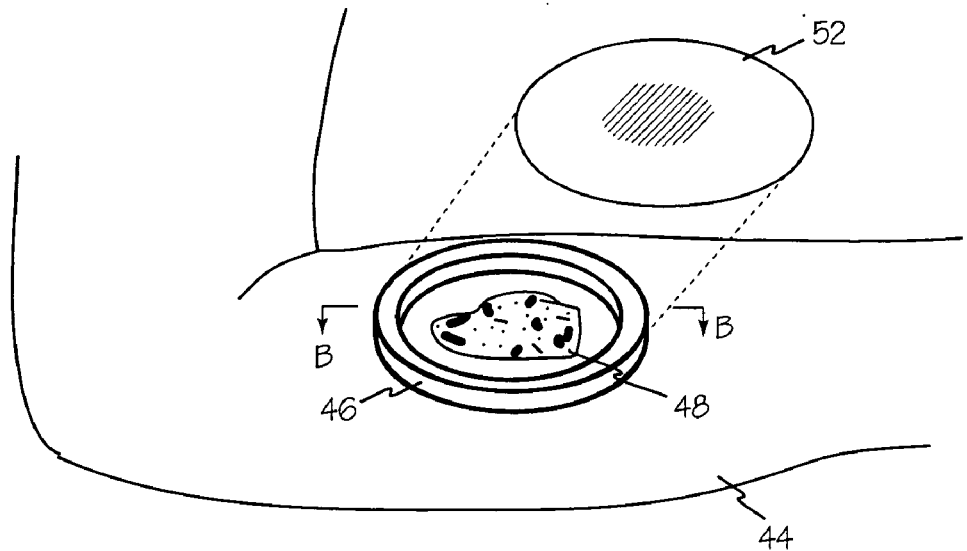
FIG. 9 is a perspective view of a frame surrounding a small wound on the forearm.

Referring to FIG. 1 and FIG. 2, frame 10 provides perimeter protection for a wound and may adapt to the contours of the wound site. Frame 10 includes exterior side 14 facing away from the wound and interior side 16 facing the wound, superficial surface 12 for engaging dressings and cutaneous surface 18 in contact with the patient's skin, or any other dressing or apparatus in contact with the patient's skin. Any suitable adhesive may be applied to cutaneous surface 18 and or superficial surface 12 such as adhesive 28 and 22 respectively. Adhesive layers 22 and 28 may also be covered by a strip or a film, such as film 24 and 26 respectively, that can be peeled off at the time of use. Adhesive 28 secures frame 10 to skin surrounding a wound, or in some applications, to a dressing or apparatus that is in contact with the patient's skin. When applied to superficial surface 12, adhesive layer 22 may engage a dressing or other suitable cover to frame 10.

In use, frame 10 completely circumscribes a wound as shown in FIG. 9. Frame 10 may have any suitable span 31 and a suitable cross-section as shown in FIG. 2 including height 30 and width 32. The size of a wound site to be circumscribed may require height 30 and width 32 to be available in different dimensions. Larger wounds may have a dressing sag and inadvertently contact the wound. Height 30 and span 31 and the characteristics of a dressing may be selected and considered to minimize inadvertent dressing to wound contact.

Frame 10 may be constructed from any suitable material such as for example, silicone; polymers such as polypropylene, polyethylene and polyurethane may also be used to form a suitable wound protector. Depending on its specific use, additional features of a wound shield may include impermeability or controlled permeability to water, bacteria and air, and absorption of fluids exuding from the wound bed. A wound shield according to the present disclosure may also include a selectable moisture vapor transmission rate (MVTR). Polyurethane foam may be used to form a wound-protecting frame for its ability to absorb exudates.

Referring now to FIGS. 3-5, frame 10 may adopt any suitable cross section.

Referring now to FIGS. 6, 7 and 8 alternatively, a frame such as frame 34, 36 or 38 may have any suitable shape or geometry.

Figure 10:
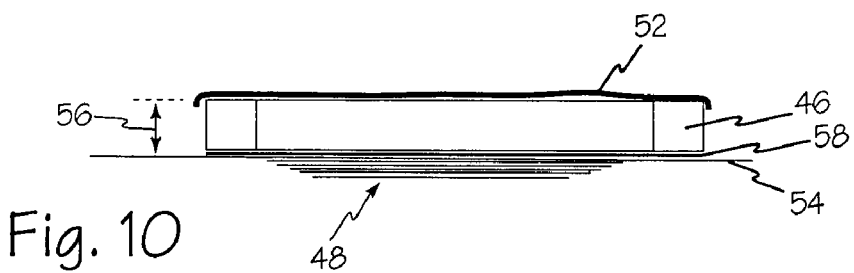
FIG. 10 is a cross section of the frame and dressing on the wound of FIG. 9.

Referring now to FIG. 9 and FIG. 10, frame 46 may be applied to any surface of a patient such as forearm 44 using adhesive 58. Frame 46 circumscribes wound 48. When dressing 52 is used to promote healing of wound 48, frame 46 prevents dressing 52 from contacting wound 48 by creating a separation 56 between dressing 52 and wound plane or skin surface 54. Separation 56 is controlled by height 30 of the frame.

As briefly described above, dressing 52 may be any suitable dressing. Dressing 52 may also include adhesive along its perimeter or longitudinal and/or its transverse lengths, so to facilitate its adherence to skin surrounding frame 46. Alternatively, dressing 52 may be wrapped around the arm or other body parts on which wound 48 is situated, or dressing 52 may be sized or cut to size to engage only frame 46. Dressings such as dressing 52 may have any suitable MVTR parameters.

Figure 11:
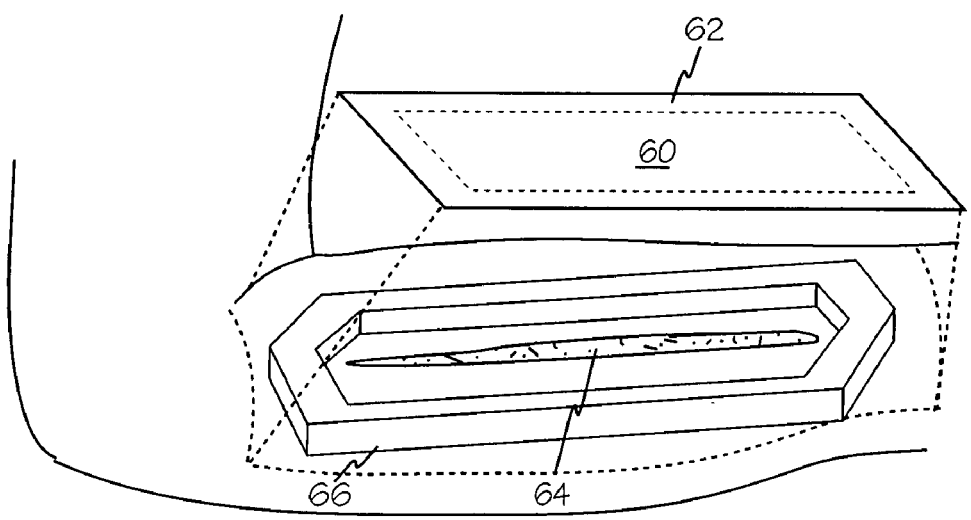
FIG. 11 is a perspective view of a frame surrounding a long, oddly shaped laceration on the forearm.

Referring now to FIG. 11, dressing 60 may be used to secure frame 66 around wound 64, which is a long, narrow, oddly shaped laceration. Adhesive may be included around perimeter 62 of dressing 60. One or more dressing such as dressing 60 may be used. Dressing 60 may be applied along the length, width, or in tandem with another dressing 60 or other dressings to protect wound 64.

Figure 12:
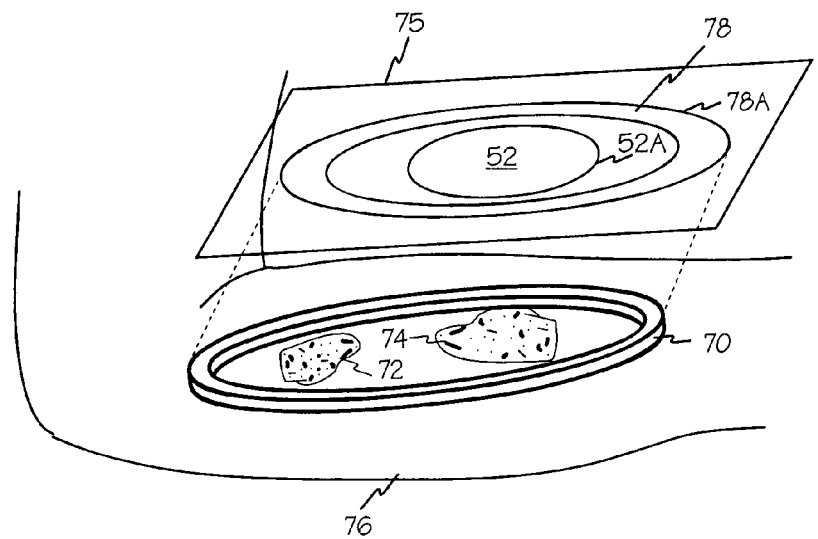
FIG. 12 is a perspective view of a wound frame surrounding two proximately located wounds on the forearm.

Referring now to FIG. 12, frame 70 may be used to protect one or more proximately located wounds such as wounds 72 and 74 on forearm 76. Dressing 78 may be separated from scored dressing sheet 75 which may have one or more dressings scored into sheet 75. Dressings such as dressing 52 or dressing 78 may be separated from sheet 75 along scoring 52A or 78A respectively. Any size or number of dressings may be pre-scored into a dressing sheet such as sheet 75.

A frame according to the present disclosure may not always completely circumscribe a wound. For wounds positioned in awkward body locations, such as the elbow and knee or for any other reason, a frame may be cut into two or more suitable lengths or frame elements to be positioned around the wound as discussed above. Such manipulation may allow positioning of a dressing without contacting the wound.

In certain circumstances health care professionals may recommend the airing of the wound, i.e., not covering the wound with any dressing. As such, a frame according to the present disclosure may be used to simply protect the wound from physical contact with other foreign objects, such as clothing or bed sheets. This configuration may also be suitable for treatment of any pressure or abrasion sores some of which may be caused by long-term immobility. A frame may be used to surround such sores and relieve the local pressure and permit the sores to heal.

For patients allergic to medically approved adhesives, the frame may be provided without adhesive or, alternatively, with adhesive only on surface 12. In such circumstances, frame 10 must be secured to the wound site with sufficient and appropriate pressure to engage frame 10 with the wound site.

For wound configurations such as illustrated in FIG. 11 and or FIG. 12, particularly large wounds, structurally weak dressings or high pressure wound or sore sites it may be necessary to provide additional support within the perimeter of a frame to support the selected dressing or relieve external pressure.

Figure 13:
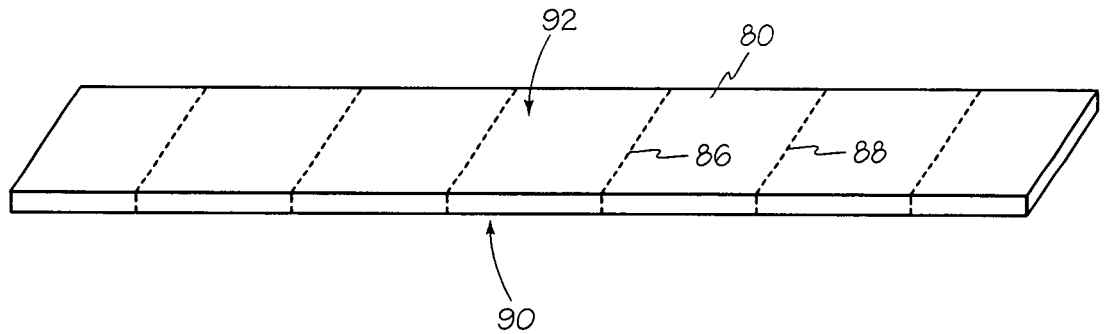
FIG. 13 is a perspective view of a support or bridge member according to the present disclosure.
Figure 15:
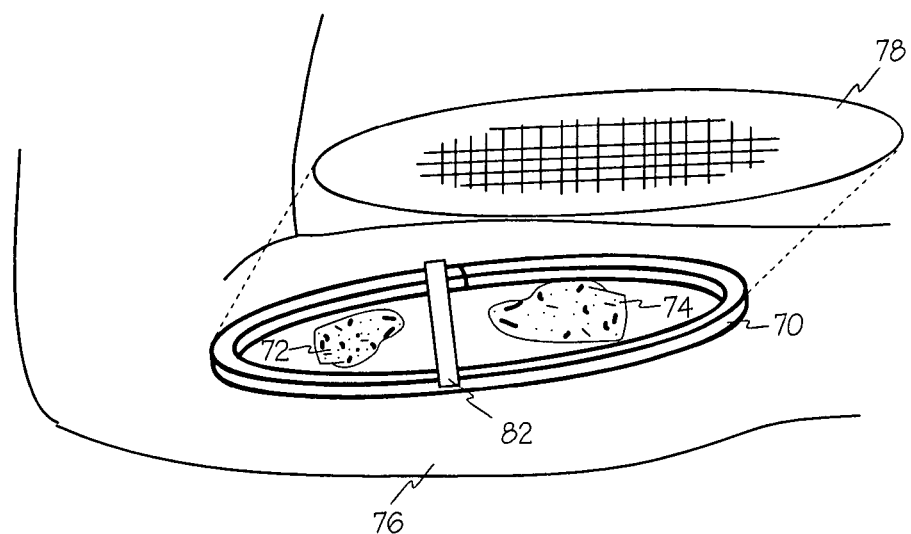
FIG. 15 is a perspective view of a wound frame surrounding two proximately located wounds on the forearm.

Referring now to FIG. 13, one or more bridge members such as bridge member 80 may be used with the frame of the present disclosure to provide additional wound protection. A bridge member may be used with wounds having large surface area or with dressings having little structural strength, or in situations where pressure may be applied to the center of the wound area. Positioning of one or more bridge members such as bridge 82 on frame 70, as depicted in FIG. 15, may prevent dressing 78 from sinking and touching wounds 72 or 74.

A bridge member can have any suitable shape including straight or curved edges, ends or separations. A bridge may also be constructed from inexpensive medical grade rigid plastic polymers, metal or wood particularly conditioned for medical use. Such material may be structurally adapted to allow breakage or separation along segment lines such as lines 86 and 88.

Medical grade adhesive may also be applied to second surface 90 which will come in contact with the frame. A thin layer of film or strip removable at time of use may cover the adhesive as discussed above with respect to the frame. Alternatively, bridge member 80 may have adhesive on both second side 90 and first side 92 to adhere not only to the frame, but also to the dressing.

Figure 14:
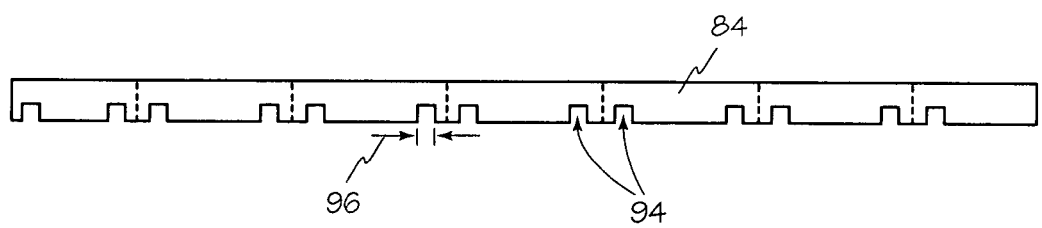
FIG. 14 is a side view of an alternate support or bridge member according to the present disclosure.

Referring now to FIG. 14, alternate bridge member 84 includes a plurality of slots 94. Each slot or opening such as slot 94 may have any suitable shape and dimension providing that width 96 is sized to permit engagement of a suitable frame in the slot.

Figures 16, 17:
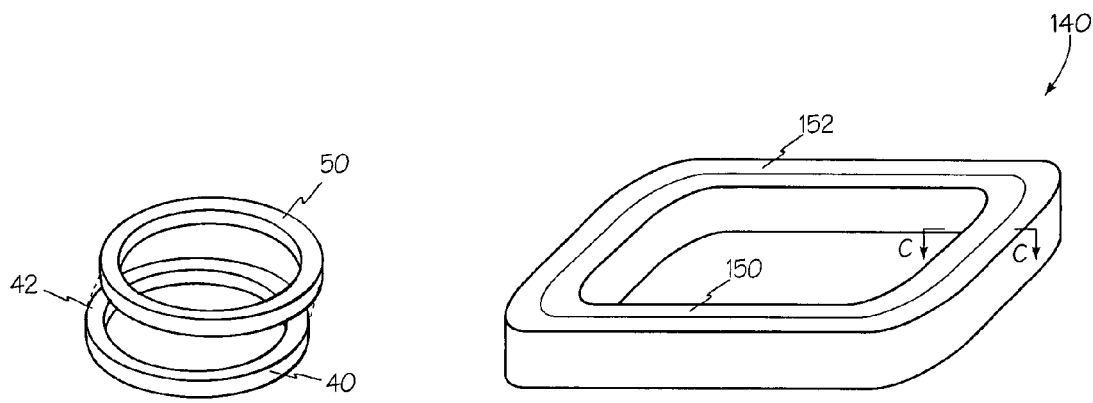
FIG. 16 is a perspective view of an alternate flexible wound frame according to the present disclosure.
FIG. 17 is a perspective view of an alternate flexible wound frame according to the present disclosure.

Referring to FIG. 16, a second frame 50 may be positioned on superficial surface 42 of a first frame 40. This configuration may be used in situations where a greater protective height around a wound is preferable. A stacked assembly may include more than two frames.

Referring now to FIG. 17 and FIG. 18, frame 140 may have many different cross sectional dimensions as well as constituent configurations. Frames as discussed above may adopt any suitable geometry. For some applications it may be useful for a frame to be composed of two or more internal layers such as layers 150 and 152 illustrated in FIG. 18. For example, layer 150 may be absorbent, or may include any suitable antibiotic such as for example silver metal and or its salts. Layer 152 may be made from any suitable material.

In some situations it may be preferable to change one or more layers closest to a wound when the layer or layers become saturated or otherwise unsuitable to remain close to the wound. Layer 150 may be removable to permit changing one or more layers. A scaffold or other suitable apparatus such as scaffold 138 may be secured to exterior layer 152. Internal layer 150 may be secured or otherwise engaged to either or both layer 152 and scaffold 138.

Internal layer 150 may be positioned and secured using scaffold 138. Securing layer 150 to layer 152 and scaffold 138 using water soluble adhesive would simplify removal of layer 150 and may also serve to identify a saturated layer as it separates from the structural layer and the scaffold. If layer 150 needed to be changed, any dressing or lid applied over frame 140 may be disengaged. Layer 150 may be removed and a replacement layer may be inserted using scaffold 138 as a guide and engagement mechanism.

Referring now to FIG. 19, an alternate scaffold 139 may include lip 141 to frictionally engage layer 150 without the use of adhesive or other bonding agent. Scaffold 138 and or scaffold 139 may also include holes or other suitable openings such as holes 135 and 143 and openings 145 in shelf 133 and or lip 141 as illustrated in the associated close-up bottom views. Lip 141 may also permit usage and of any suitable absorbent material in a non-contact position relative to the wound. The absorbent material may be frictionally engaged by lip 141 and supported by scaffold 139.

Some materials may have directional characteristics, and when combined in multiple layers may offer unique benefits. Many additional characteristics may also be useful, for example, layer 156 of FIG. 20 may be absorbent to absorb and retain exudate from the wound, and layer 154 may be formed of a material providing dimensional stability or structural integrity.

Similarly, referring to FIG. 22, layer 164 may be absorbent and layer 166 may provide structural integrity and layer 166 may enclose layer 164 to prevent exudates from wound side 144 transiting frame 140 and exiting through exterior side 146. Any suitable material may be selected for each layer. Layer 168 may be any suitable material.

Referring now to FIG. 21, layers 158, 160 and 162 may also provide one or more diagnostic indicators such as for example, ph level, temperature, moisture level, $O^2$ levels or any other suitable parameter. The state of the parameter may be indicated by one or more color states of one or more layers.

Referring now to FIG. 23, frame 170 may include one or more internal layers such as layers 172, 174 and 176 and one or more absorbent appendages such as arm 178. Arm 178 and layer 176 may be composed of any suitable material for absorbing exudates from wound 180. The physical geometry of arm 178 may vary for varying applications. For example, arm 184 shown in FIG. 24 provides vertical relief from wound 180.

Alternatively as illustrated in FIG. 25, flexible absorbent appendages may also be secured to a frame such as frame 192. Absorbent appendages 194 may be provided to absorb exudate from wound 180. Any suitable material or combination of materials may be used as appendages 194 such as for example natural fibers such as cotton or any suitable man-made fiber such as polyurethane foam. Any other suitable configuration may also be employed such as enclosing one or more cotton balls or gauze within the space enclosed by a frame and a covering dressing.

Figure 26:
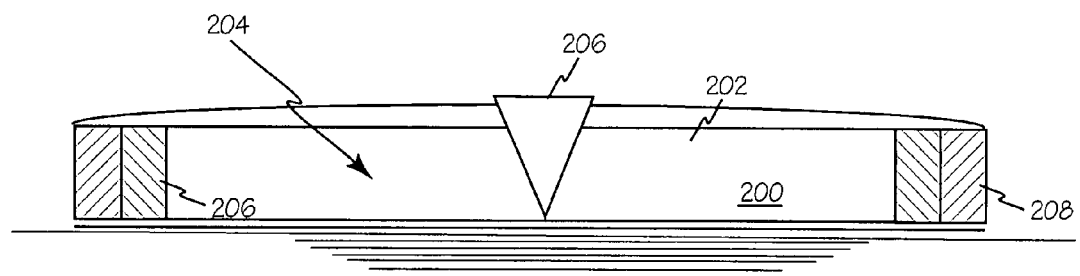
FIG. 26 is a cross section of an alternate frame and lid configuration.

Referring now to FIG. 26, frame 200 may also be used with a cover or lid 202 to provide a controlled environment in enclosed space 204 adjacent a wound site. Lid 202 may be removably engaged to frame 200 using any suitable technique such as frictional or adhesive engagement. Lid 202 may be formed of any suitable material or combination of materials such as a structural grid layer with one or more laminate layers to obtain suitable performance and moisture transmission/retention.

Alternatively, lid 202 may also include one or more absorptive elements such as cone 206 for removing moisture or exudate from wounds such as wound 210. Absorptive elements may have any suitable shape or dimension and may be formed of any suitable material. For example, cone 206 may be formed of material that is selectively absorbent to remove exudate and unwanted fluids.

Figure 27:
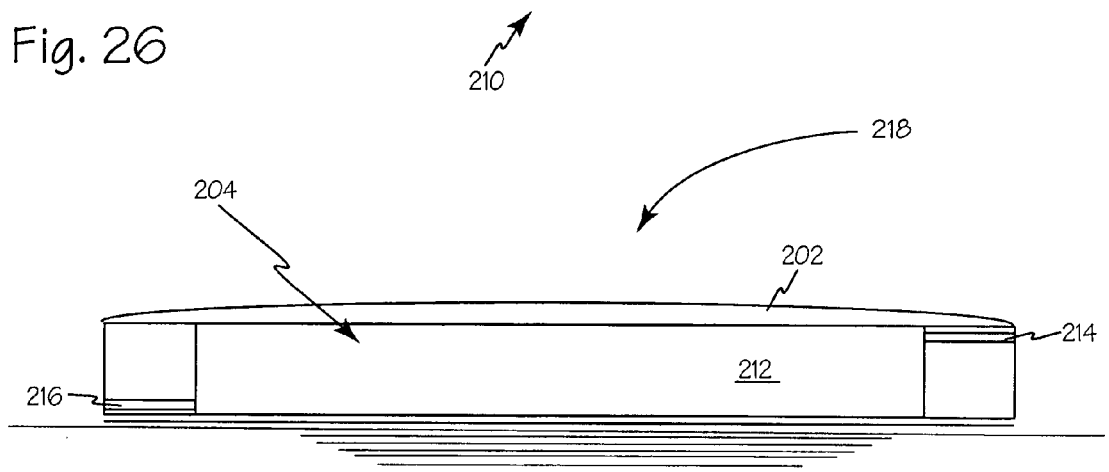
FIG. 27 is a cross section of another alternate frame and lid configuration.

Enclosed space 204 may be further controlled as illustrated in FIG. 27. Frame 212 may include one or more access ports such as inlet port 214 and outlet port 216. Use of access ports permits irrigation, treatment, and or debridement of wound 210 without removing wound protection shield 218. Fluid or other material may be introduced into enclosed space 204 through inlet port 214. In the case of used fluid or exudate, removal may be accomplished using outlet port 216. Access ports such as inlet port 214 and outlet port 216 may be reclosable to secure enclosed space 204. Alternatively, frame 212 may be formed of material that permits a syringe to be inserted through the frame for insertion of material or to remove material. Access ports may also be formed in the cover or lid 202.

Figure 28:
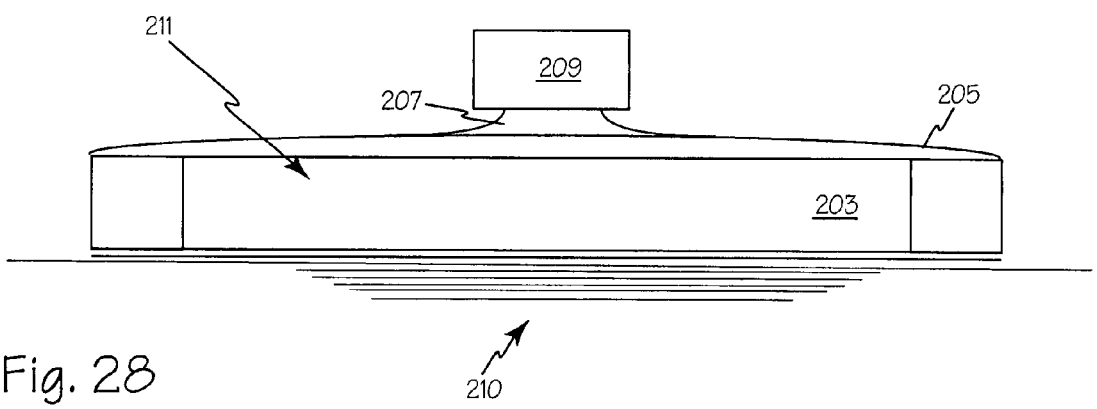
FIG. 28 is a cross section of a frame with a vacuum lid configuration.

Referring now to FIG. 28 enclosed vacuum space 211 may be created and maintained by the use of a suitable cover or lid such as vacuum lid 205. A partial or complete vacuum may be created in space 211 by vacuum device 209 through adapter 207 or through a frame such as frame 212 using inlet port 214 or outlet port 216. Using a frame and specifically adapted lid such as lid 205 may permit a vacuum device such as vacuum device 209 to be located on lid 205 without creating unsatisfactory pressure on or adjacent wound 210. Lid 205 may require an adapter such as adapter 207 or lid 205 may be specifically formed to adapt to a vacuum device or connector to a vacuum device to create a full or partial vacuum within space 211.

Figure 29:
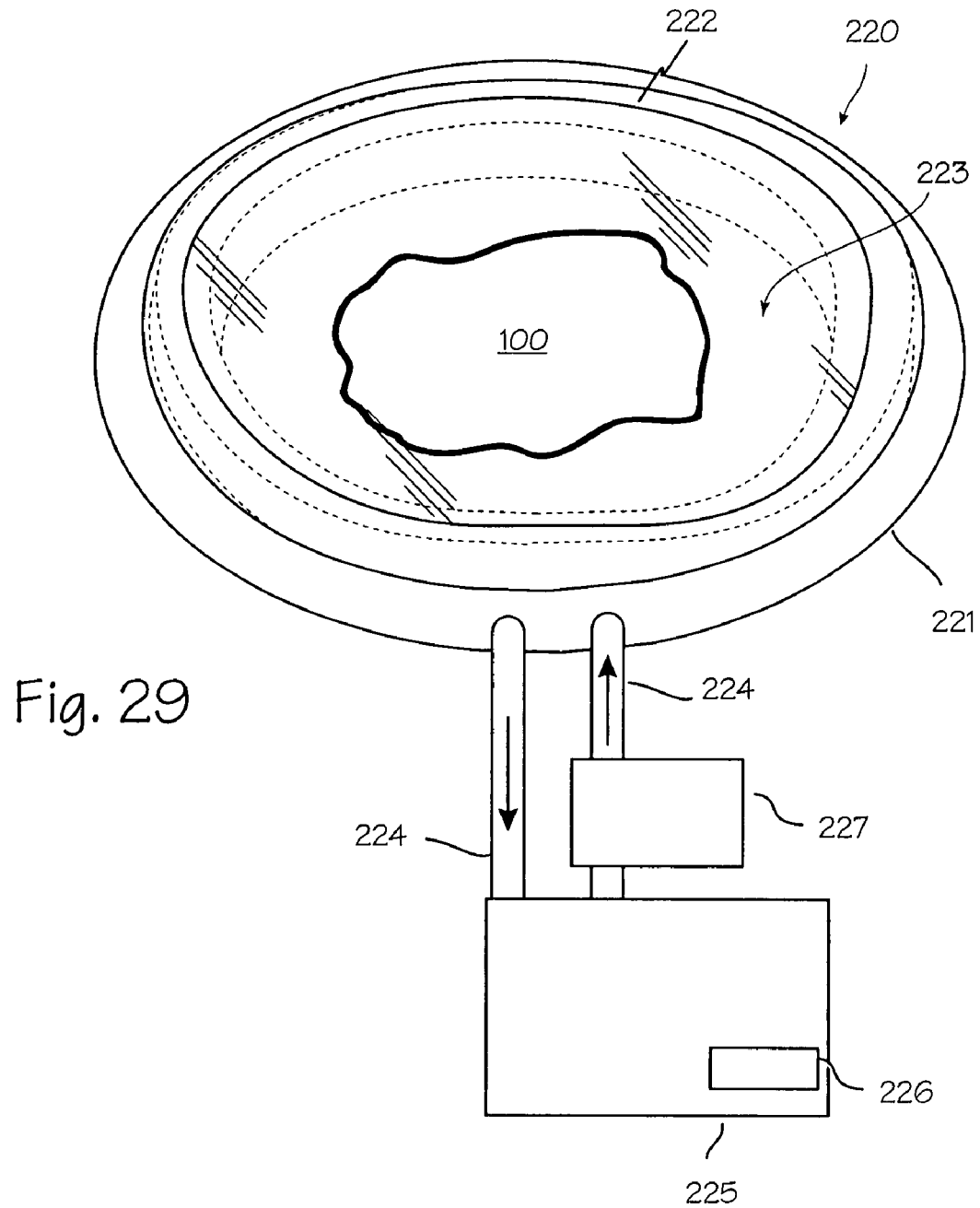
FIG. 29 illustrates a device for isolating a wound and providing heat to the wound to encourage healing.

FIG. 29 illustrates the wound isolation and warming device 220, including tube 221, inner absorbent ring or strip 222 and breathable vapor barrier 223. The tube and absorbent strip are provided with any suitable adhesive on the cutaneous surfaces of the tubing, the strip, or both, to secure the device to the skin of a patient. The tubing is made of polyethylene or other thermally conductive material, and may either be bent and formed as necessary to adapt to the contours of a patient's body. The device also includes water supply and return conduits 224, and a warm water source 225 comprising a water reservoir, heater 226 (or any other suitable heating means), pump 227, and appropriate thermostats, heating regulators and flow regulators. Pulsatile flow can be provided with roller pump or centrifugal pulsatile flow pump. The heater and thermostat are preferably operable to maintain water temperature at a therapeutic temperature of about 105° F. (about 36-39° C.), but may be operated to maintain higher or lower temperatures as medically indicated. The device is illustrated in place surrounding wound 100 on the skin of a patient.

Figure 30:
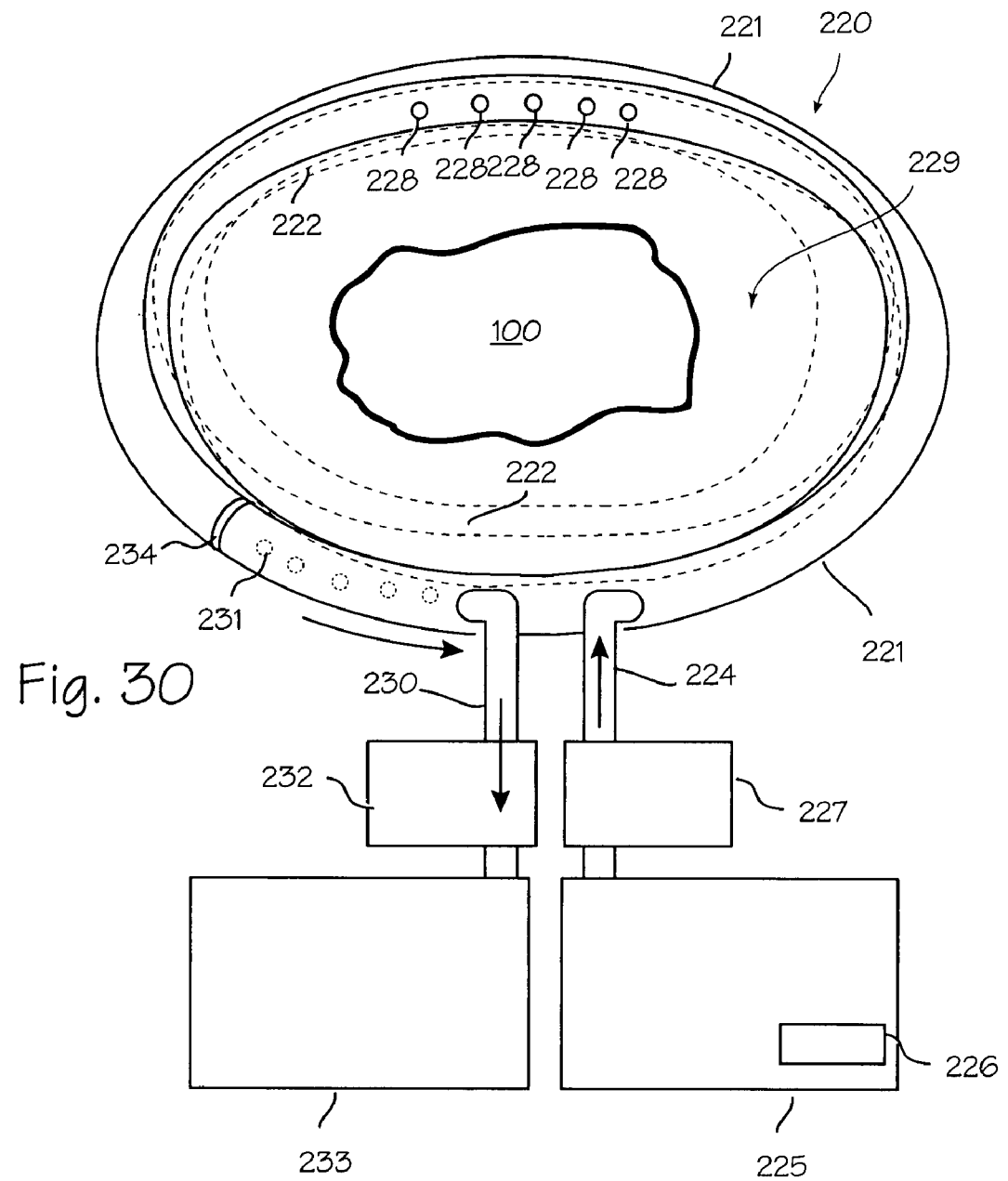
FIG. 30 illustrates the device of FIG. 29 modified to provide fluid flow over the wound to encourage healing.

The device may be modified as shown in FIG. 30, in which the tube 221 in the vicinity of the wound is perforated, such that apertures 228 distributed along the inner wall of tubing 221 and any intervening portion of frame 222 direct water into the interior space 229 (defined by the frame) and onto the wound. Water is collected through return tube 230 through suction ports 231 and appropriate suction pump 232 and collected in wastewater tank 233. Water may be collected through a discrete segment of the tube formed integrally with an interior wall or plug 234 provided to isolate the supply and suction tubes. Alternatively, the suction tube may be butt-joined with the supply tube. Used fluid may also be collected with a second, discrete suction tube, or through an additional lumen and ports in the first tube.

Tube 221 may be made or formed in any cross section shape including but not limited to cylindrical, rectangular, trapezoidal or any other suitable shape. A suitable shape of tube 221 may be selected to control the flow of thermal energy around the wound, generally to increase the temperature of the wound site, however cooling may also be provided. Tube 221 may also include one or more insulating layers to control the thermal energy and prevent unwanted losses. Adhesive may also be used as necessary on tube or its adjacent surfaces to secure tube 221 in use.

In use, the devices of FIGS. 29 and 30 are applied to a patient so that the tubing substantially circumscribes a wound, and fixed to the skin of the patient with adhesives on the cutaneous surfaces of the tubing and absorbent ring (or secured with bandages, wherever adhesives are inadequate or inappropriate). The pump and heater are operated to maintain warm fluid flow through the tube, to maintain a warm environment proximate the wound. In the closed system of FIG. 29, the fluid is returned to reservoir, reheated and re-circulated through the system. When using the device of FIG. 30, the suction pump is operated to draw fluid from the wound environment and deliver that fluid to the wastewater tank. Therapeutic agents such as antibiotics may be added to the warm water source when medically indicated.

Referring to FIG. 31, absorbent layer 164 may be oriented to be out of contact with the patients skin. Absorbent layer 164 may be configured to absorb and or store exudate from a wound. Relief such as relief 240 isolates the absorbed exudate away from the patients skin. Relief 240 may be selected to be any suitable dimension.

Dynamic exudate management and removal may be provided by layer 242 of FIG. 32. The material of layer 242 is selected to flex when new and to extend over relief 244 and contact the surface of a wound to engage exudate. Upon absorbing exudate, layer 242 will contract to draw exudate across relief 244 to continue wicking exudate from the wound with absorbent layer 242 out of contact with the wound or the patients skin.

Referring to FIG. 33, exudate 246 may be conducted from wound 210 and enclosed space 258 with alternate frame 248. The material of layer 250 may be selected to perform as a conduit by drawing exudate 246 from wound 210 and transferring exudate 246 to one or more storage layers of dressing 252 such as layer 254. Layer 250 will not retain exudate 246. Absorbent layer 254 may be any suitable material and may also be expandable. Area 256 of dressing 252 may permit viewing of wound 210 and may have a selected permeability to enhance control of enclosed space 258.

Figure 34:
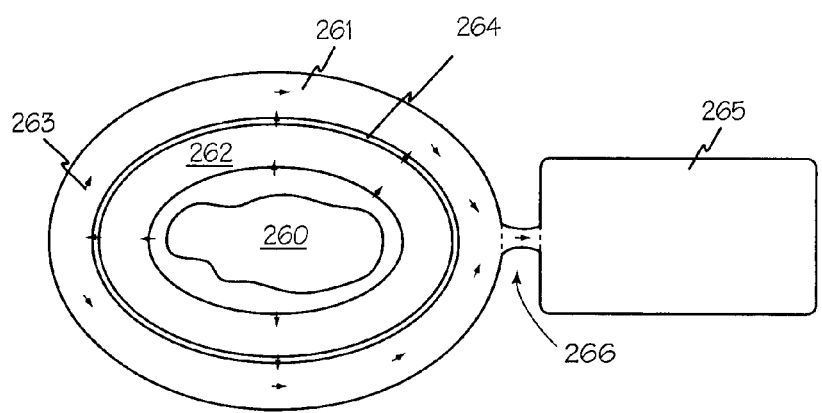
FIG. 34 is a cross section of an alternate frame configuration including exudate capture and storage.

Wound 260 of FIG. 34 may produce exudate 263. An alternate frame 262 may conduct exudate away from wound 260. Membrane 264 may surround frame 262 or may otherwise be included as a layer of frame 262. Membrane 264 may allow exudate to pass in only one direction, away from the wound. Once exudate 263 has passed membrane 264 it may be absorbed or otherwise conducted along drain 261 away from the wound. Drain 261 may include an access port 266 which may accommodate continuous or intermittent connection for withdrawal or drainage of exudate from drain 261 into reservoir 265. Reservoir 265 may be adjacent to wound 260 or may be remotely located by interconnecting reservoir 265 to drain 261 with a tube or other suitable element. Alternatively, reservoir 265 may be used to introduce water or other suitable solvent or cleanser into drain 261 to expedite removal of exudate 263.

Figure 35:
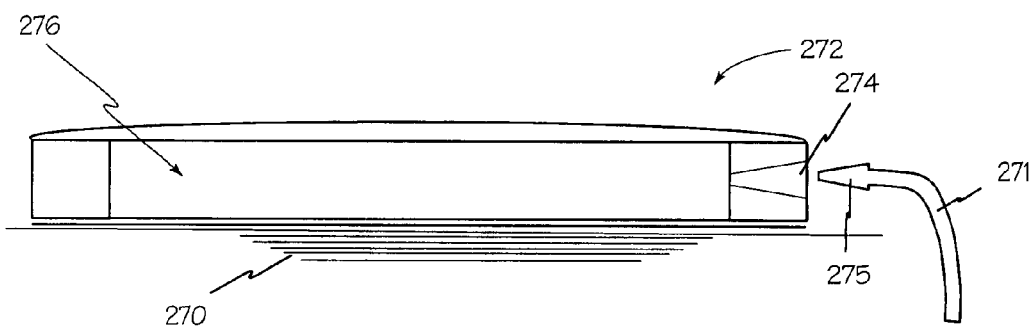
FIG. 35 is a cross section of an alternate frame configuration including exudate removal apertures and removal apparatus.

Referring now to FIG. 35, use of access ports permits exudate management with irrigation, treatment, and or debridement of a wound such as wound 270 without removing wound protection shield 272. Fluid and or other material may be introduced, and exudate, fluid and or other material may be removed from enclosed space 276 through port 274. Access ports such as port 274 may adopt any suitable geometry for engaging various tubes, such as tube 271, syringes, and devices such as reservoir 273. Ports may be reclosable using any suitable technique to secure enclosed space 276.

Adapters such as adapter 275 may engage port 274 to permit leak proof access to enclosed space 276. As adapter 275 enters port 274 the port is opened, and as adapter 275 is withdrawn port 274 closes and withdrawal of an adapter cleanses port 274.

Figure 36:
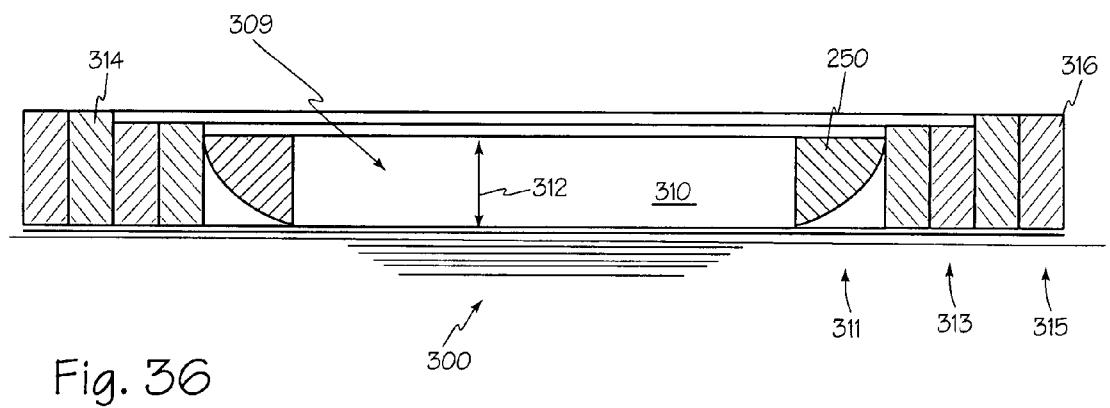
FIG. 36 is a cross section of an alternate frame configuration with circumferential steps of varying heights.

Referring now to FIG. 36, conformable frame 310 may have a step varying height 312 from inner step 311 which has the lowest height 312 and subsequent steps such as steps 313 and 315 have increasing heights. The height variations may be distinct such as steps, or it may be gradual and continuous as shown in conformable frame 320 of FIG. 37. The height variations distribute pressure that might otherwise impact the wound, to surrounding tissue removed from the wound. As pressure increases compressing outer wraps of conformable frame 310, the inner wraps begin to provide support increasing pressure resistance. Conformable frame 310 may be formed of one or more layers 314 and or 316 as discussed above, and may also include a conduit layer 250 adjacent to wound 300 and forming the perimeter of wound space 309.

Figure 37:
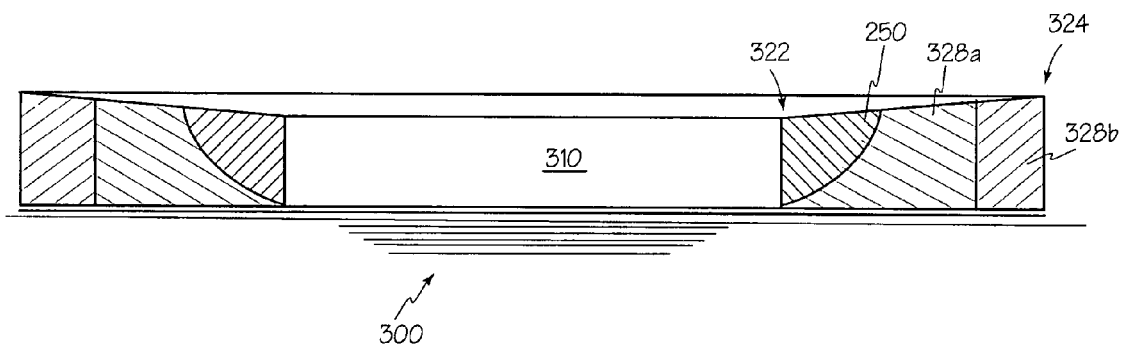
FIG. 37 is a cross section of an alternate frame configuration having a radially varying thickness.

Conformable frame 320 of FIG. 37 illustrates a continuously increasing height from inner edge 322 to outer edge 324. Characteristics of conformable frame 320 may change gradually and continuously from first end 322 to second end 324 or there may be one or more zones such as zones 328a and 328b. Each zone may have different compression resistance, absorbance or any other suitable characteristics.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A shield for protecting a wound, the shield comprising:
    a conformable frame having a preformed shape to circumscribe the wound, the preformed shape comprising a preformed cross-section, a preformed span, and a preformed geometry;
    a first adhesive layer securing the conformable frame around the wound;
    a lid engaging the conformable frame to enclose a space about the wound, the lid configured to allow for moisture transmission;
    a second adhesive layer securing the lid to the conformable frame; and
    one or more access ports through the conformable frame for removal of material from the enclosed space.

2. The shield of claim 1 wherein the conformable frame comprises:
    an absorbent layer for absorbing wound exudate.

3. The shield of claim 2 wherein the conformable frame further comprises:
    an additional layer, an interface between the absorbent layer and the additional layer being oriented perpendicular to a surface of the wound.

4. The shield of claim 2 wherein the conformable frame further comprises:
    an additional layer, an interface between the absorbent layer and the additional layer being oriented parallel to a surface of the wound.

5. The shield of claim 1, further comprising:
    one or more absorbent extremities extending into the enclosed space.

6. The shield of claim 5 where the one or more absorbent extremities comprise polyurethane foam.

7. The shield of claim 5 where the one or more absorbent extremities are formed integral to the conformable frame.

8. The shield of claim 1, wherein the lid comprises an exudate absorbing material, the conformable frame configured to transport exudate from the wound to the lid.

9. A method of shielding a wound on a patient, the method comprising:
    selecting a preformed conformable frame to circumscribe a wound, the conformable frame having a preformed cross-section, a preformed span, a preformed geometry, and an access port to remove material from the wound;
    adhering the preformed conformable frame around the wound;
    after adhering the preformed conformable frame around the wound, securing a moisture permeable dressing to the conformable frame so as to enclose a space about the wound; and
    removing material from the enclosed space via the access port.

10. The method of claim 9, wherein the moisture permeable dressing comprises an exudate absorbing material, the conformable frame configured to transport exudate from the wound to the dressing.

* * * * *